US012805815B2

(12) United States Patent
Kiji et al.

(10) Patent No.: US 12,805,815 B2
(45) Date of Patent: Nov. 24, 2026

(54) PHOTON COUNTING CT APPARATUS AND MEDICAL IMAGE PROCESSING METHOD

(71) Applicant: CANON KABUSHIKI KAISHA, Tokyo (JP)

(72) Inventors: Hiroaki Kiji, Utsunomiya (JP); Hiroki Taguchi, Otawara (JP); Yohei Minatoya, Bunkyo (JP); Masakazu Matsuura, Nasushiobara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 204 days.

(21) Appl. No.: 18/748,716

(22) Filed: Jun. 20, 2024

(65) Prior Publication Data

US 2024/0423560 A1 Dec. 26, 2024

(30) Foreign Application Priority Data

Jun. 22, 2023 (JP) ................................ 2023-102808

(51) Int. Cl.
*A61B 6/03* (2006.01)
*A61B 6/00* (2024.01)
*A61B 6/42* (2024.01)

(52) U.S. Cl.
CPC ............ *A61B 6/032* (2013.01); *A61B 6/4241* (2013.01); *A61B 6/5258* (2013.01)

(58) Field of Classification Search
CPC ...... A61B 6/032; A61B 6/4241; A61B 6/5258
See application file for complete search history.

(56) References Cited

U.S. PATENT DOCUMENTS

| | | | | |
|---|---|---|---|---|
| 2017/0273640 A1* | 9/2017 | Danielsson | .............. | A61B 6/03 |
| 2020/0196973 A1 | 6/2020 | Zhou et al. | | |

FOREIGN PATENT DOCUMENTS

| | | | | |
|---|---|---|---|---|
| CN | 118303903 A * | 7/2024 | ............. | G06T 12/10 |
| EP | 2046203 B1 * | 9/2017 | ............. | A61B 6/585 |
| JP | 2020-99667 A | 7/2020 | | |

OTHER PUBLICATIONS

Persson, Mats, and Hans Bornefalk. "A framework for evaluating threshold variation compensation methods in photon counting spectral Ct." IEEE transactions on medical imaging 31.10 (2012): 1861-1874. (Year: 2012).*

(Continued)

*Primary Examiner* — Uzma Alam
*Assistant Examiner* — Richard O Toohey
(74) *Attorney, Agent, or Firm* — Oblon, McClelland, Maier & Neustadt, L.L.P.

(57) ABSTRACT

A photon counting CT apparatus of an embodiment includes processing circuitry. The processing circuitry is configured to perform first determination processing of determining spike components in a counting image generated on the basis of sum data of photon detection results for a plurality of different X-ray energy bands and second determination processing of determining ring artifacts on the basis of a plurality of energy images generated on the basis of a photon detection result for each of the plurality of different X-ray energy bands, and remove or reduce ring artifacts in the counting image on the basis of both a result of the first determination processing and a result of the second determination processing.

6 Claims, 7 Drawing Sheets

(56) References Cited

OTHER PUBLICATIONS

Fang, Wei, Liang Li, and Zhiqiang Chen. "Removing ring artefacts for photon-counting detectors using neural networks in different domains." IEEE access 8 (2020): 42447-42457. (Year: 2020).*

Meier, A., et al. "Advanced virtual monoenergetic images: improving the contrast of dual-energy CT pulmonary angiography." Clinical radiology 70.11 (2015): 1244-1251. (Year: 2015).*

* cited by examiner

PHOTON COUNTING CT APPARATUS AND MEDICAL IMAGE PROCESSING METHOD

CROSS-REFERENCE TO RELATED APPLICATION

The present application claims priority based on Japanese Patent Application No. 2023-102808 filed Jun. 22, 2023, the content of which is incorporated herein by reference.

FIELD

Embodiments disclosed in this specification and drawings relate to a photon counting CT apparatus and a medical image processing method.

BACKGROUND

Sinogram-based and image-based methods have been proposed as techniques for removing ring artifacts that occur in CT images captured by an X-ray computed tomography (CT) apparatus. In these conventional methods, processing of determining a ring component on the basis of the degree of difference between adjacent elements or adjacent pixels using information such as detection data for each detection element or pixel values (CT values) of a CT image reconstructed from the detection data, and subtracting the ring component from the CT image (original data) is performed. At that time, if the difference between adjacent elements or adjacent pixels is greater than a predetermined threshold value, the ring component is designed such that it will not be removed upon determining that it is not caused by ring artifacts but by an object to be imaged (for example, an organ, a bone, or the like).

A photon counting detector (PCD), which is a semiconductor detector used in a photon counting computed tomography (PCCT) apparatus, has an element response (output characteristics) that is more likely to change due to heat and other factors and a difference in response between calibration and actual scanning that is more likely to occur than a conventional detector composed of a scintillator and photodiodes. For this reason, a strong ring component that does not appear in a conventional CT apparatus except when there is a failure of a detector may appear in the photon counting CT apparatus. With conventional ring artifact removal techniques, if the degree of difference between adjacent elements is large, a ring component is determined to be an object and thus cannot be removed even if the ring component is caused by ring artifacts.

DETAILED DESCRIPTION

Hereinafter, a photon counting CT apparatus and a medical image processing method of embodiments will be described with reference to the drawings.

A photon counting CT apparatus of an embodiment includes processing circuitry. The processing circuitry is configured to perform first determination processing of determining spike components in a counting image generated on the basis of sum data of photon detection results for a plurality of different X-ray energy bands and second determination processing of determining ring artifacts on the basis of a plurality of energy images generated on the basis of a photon detection result for each of the plurality of different X-ray energy bands, and remove or reduce ring artifacts in the counting image on the basis of both a result of the first determination processing and a result of the second determination processing.

First Embodiment

[Configuration of Photon Counting CT Apparatus]

Figure 1:
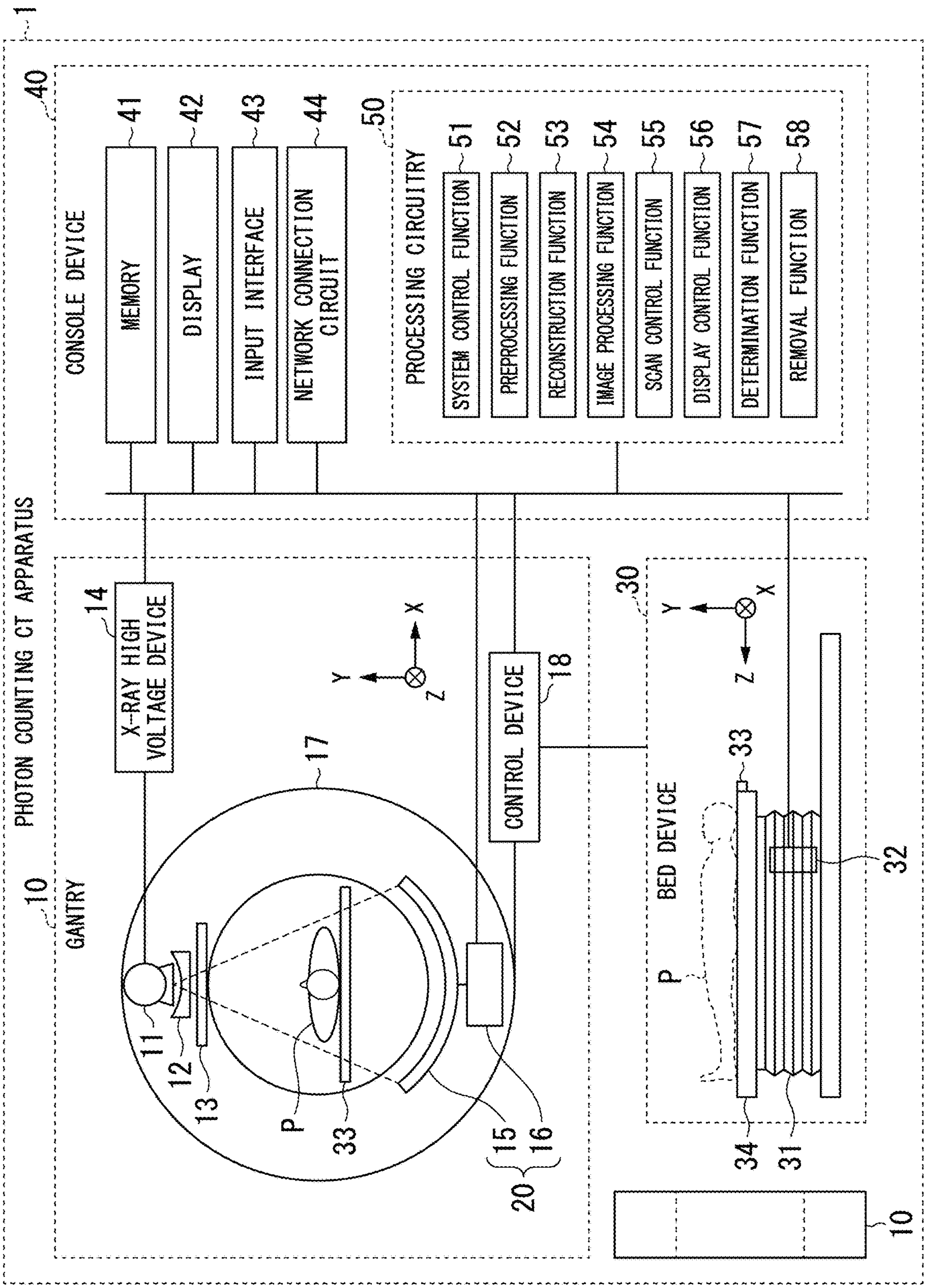
FIG. 1 is a diagram showing an example of a photon counting CT apparatus 1 according to a first embodiment.

FIG. 1 is a diagram showing an example of a photon counting CT apparatus 1 according to an embodiment. In the present embodiment, a ring artifact/object is determined using an image (hereinafter referred to as a "bin image") reconstructed for each energy band (energy bin), which is a feature of the photon counting CT apparatus, and the ring artifact is removed or reduced on the basis of the determination result. Accordingly, a CT image in which a ring artifact has been removed or reduced with high accuracy can be generated.

The photon counting CT apparatus 1 can generate image data by which a material to be examined through which X-rays have passed is discriminated using a direct detector such as a semiconductor detector with high energy resolution. The photon counting CT apparatus 1 includes, for example, a gantry 10, a bed device 30, and a console device 40. The term "photon counting CT apparatus" may refer to all of the gantry 10, the bed device 30, and the console device 40, or may refer to at least one of the gantry 10, the bed device 30, and the console device 40. Although FIG. 1 shows both a view of the gantry 10 in the Z-axis direction and a view in the X-axis direction for convenience of description, there is only one gantry 10 in reality. In the present embodiment, a rotation axis of a rotary frame 17 in a non-tilting state or the longitudinal direction of a top plate 33 of the bed device 30 is defined as the Z-axis direction, an axis orthogonal to the Z-axis direction and horizontal to the floor surface is defined as the X-axis direction, and a direction orthogonal to the Z-axis direction and perpendicular to the floor surface is defined as the Y-axis direction.

<Gantry 10>

The gantry 10 includes, for example, an X-ray tube 11, a wedge 12, a collimator 13, an X-ray high voltage device 14, an X-ray detector 15, a data acquisition system (hereinafter referred to as a DAS) 16, the rotary frame 17, and a control device 18. The X-ray detector 15 and the DAS 16 constitute a detector module 20.

The X-ray tube 11 generates X-rays by radiating thermoelectrons from a cathode (filament) toward an anode (target) by applying a high voltage from the X-ray high voltage device 14. The X-ray tube 11 includes a vacuum tube. For example, the X-ray tube 11 is a rotating anode type X-ray tube that generates X-rays by radiating thermoelectrons to a rotating anode.

The wedge 12 is a filter for adjusting the amount of X-rays radiated from the X-ray tube 11 to a subject P. The wedge 12 attenuates X-rays that pass through the wedge 12 such that the distribution of the amount of X-rays radiated from the X-ray tube 11 to the subject P becomes a predetermined distribution. The wedge 12 is also called a wedge filter or a bow-tie filter. The wedge 12 is, for example, made of aluminum processed to have a predetermined target angle and a predetermined thickness.

The collimator 13 is a mechanism for narrowing down a radiation range of X-rays that have passed through the wedge 12. The collimator 13 narrows down the radiation range of X-rays by forming a slit using a combination of a plurality of lead plates, for example. The collimator 13 may be called an X-ray diaphragm. A narrowing range of the collimator 13 may be mechanically driven.

The X-ray high voltage device 14 includes, for example, a high voltage generation device that is not shown and an X-ray control device that is not shown. The high voltage generation device has an electric circuit including a transformer, a rectifier, and the like and generates a high voltage to be applied to the X-ray tube 11. The X-ray control device controls the output voltage of the high voltage generation device depending on the amount of X-rays to be generated in the X-ray tube 11. The high voltage generation device may boost a voltage using the aforementioned transformer or using an inverter. The X-ray high voltage device 14 may be provided on the rotary frame 17 or may be provided on the side of a fixed frame (not shown) of the gantry 10.

The X-ray detector 15 detects the intensity of X-rays that enters after being generated by the X-ray tube 11 and passing through the subject P. The X-ray detector 15 outputs an electrical signal (an optical signal or the like) corresponding to the detected intensity of X-rays to the DAS 16. The X-ray detector 15 has, for example, a plurality of X-ray detection element rows. Each of the plurality of X-ray detection element rows has a plurality of X-ray detection elements arranged in a channel direction along an arc having the focal point of the X-ray tube 11 as a center. The plurality of X-ray detection element rows are arranged in a slice direction (row direction).

The X-ray detector 15 is, for example, a direct detection type detector. As the X-ray detector 15, for example, a semiconductor diode having electrodes attached to both ends of a semiconductor is applicable. X-ray photons incident on a semiconductor are converted into electron-hole pairs. The number of electron-hole pairs generated according to incidence of one X-ray photon depends on the energy of the incident X-ray photon. Electrons and holes are attracted to a pair of electrodes formed at both ends of the semiconductor. The pair of electrodes generate electric pulses having peak values depending on the charge of electron-hole pairs. One electric pulse has a peak value that corresponds to the energy of the incident X-ray photon.

The DAS 16 collects count data indicating the number of counts of X-ray photons detected by the X-ray detector 15 for a plurality of energy bins, for example, in accordance with a control signal from the control device 18. The count data regarding the plurality of energy bins corresponds to the energy spectrum with respect to X-rays incident on the X-ray detector 15, which has been modified according to response characteristics of the X-ray detector 15. The DAS 16 outputs detection data based on digital signals to console device 40. The detection data is a digital value of count data identified by the channel number and the row number of an X-ray detection element that is a generation source, and a view number indicating a collected view. A view number is a number that changes as the rotary frame 17 rotates, and is a number that is incremented as the rotary frame 17 rotates, for example. Therefore, the view number is information indicating a rotation angle of the X-ray tube 11. A view period is a period that falls between a rotation angle corresponding to a certain view number and a rotation angle corresponding to the next view number.

The DAS 16 may detect switching of views using a timing signal input from the control device 18, an internal timer, or a signal obtained from a sensor that is not shown. When the X-ray tube 11 is continuously emitting X-rays during full scanning, the DAS 16 collects a group of detection data for the entire circumference (360 degrees). When the X-ray tube 11 is continuously emitting X-rays during half scanning, the DAS 16 collects detection data for half the circumference (180 degrees). The DAS 16 processes detection data detected by the semiconductor detector.

Figure 2:
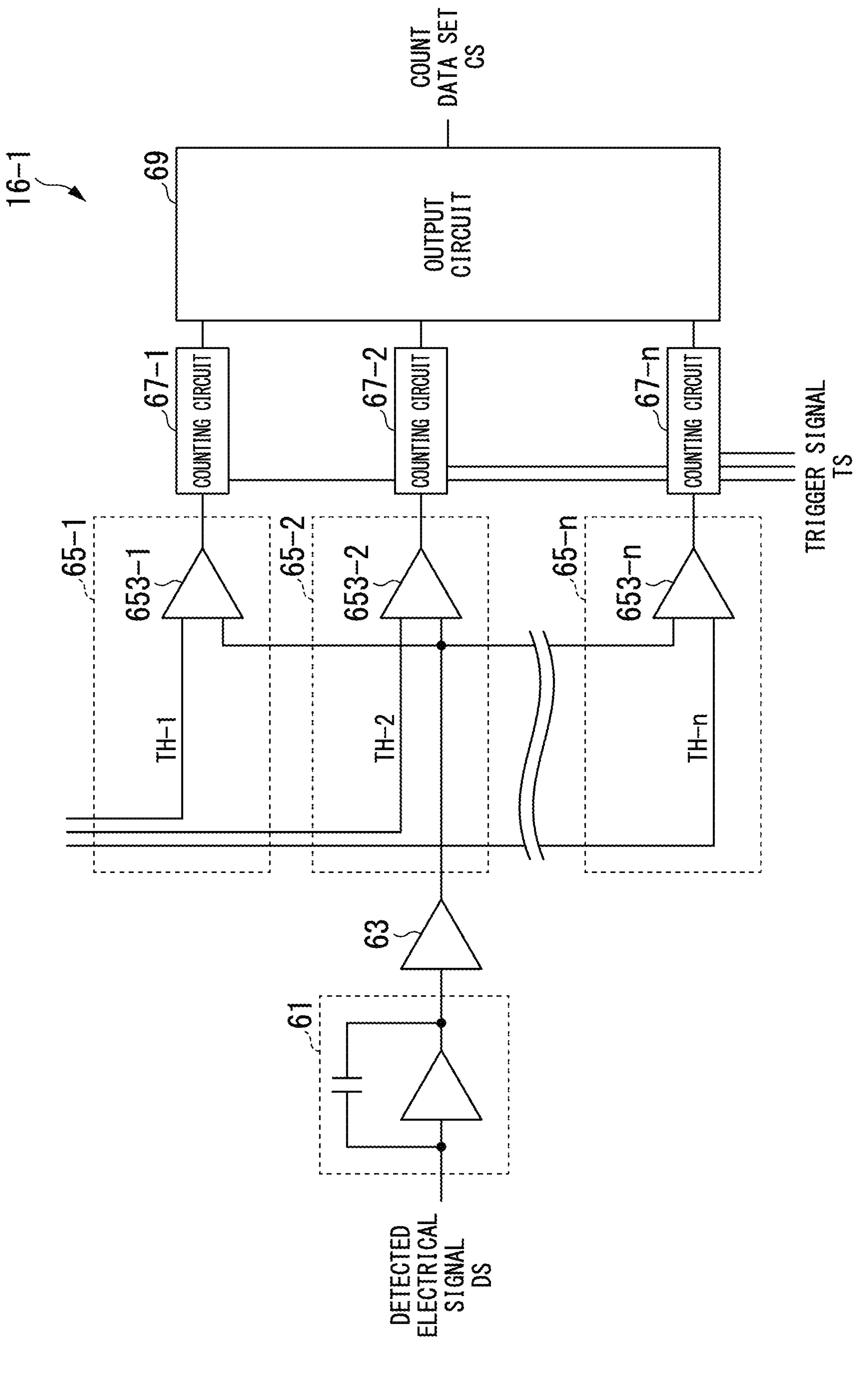
FIG. 2 is a diagram showing an example of a configuration of a DAS 16 according to the first embodiment.

FIG. 2 is a diagram showing an example of a configuration of the DAS 16 according to the first embodiment. The DAS 16 includes readout channels corresponding to the number of X-ray detection elements. These readout channels are implemented in parallel on an integrated circuit such as an ASIC. FIG. 2 shows only the configuration of a DAS 16-1 for one readout channel.

The DAS 16-1 includes a preamplifier circuit 61, a waveform shaping circuit 63, a plurality of pulse height discrimination circuits 65, a plurality of counting circuits 67, and an output circuit 69. The preamplifier circuit 61 amplifies a detected electrical signal DS (current signal) from a connected X-ray detection element. For example, the preamplifier circuit 61 converts a current signal from the connected X-ray detection element into a voltage signal having a voltage value (peak value) proportional to the amount of charge of the current signal. The waveform shaping circuit 63 is connected to the preamplifier circuit 61. The waveform shaping circuit 63 shapes the waveform of the voltage signal from the preamplifier circuit 61. For example, the waveform shaping circuit 63 reduces the pulse width of the voltage signal from the preamplifier circuit 61.

A plurality of counting channels corresponding to the number of energy bands (energy bins) are connected to the waveform shaping circuit 63. When n energy bins are set, the waveform shaping circuit 63 is provided with n counting channels. Each counting channel has a pulse height discrimination circuit 65-*n* and a counting circuit 67-*n*.

Each of the pulse height discrimination circuits 65-*n* discriminates the energy of X-ray photons detected by the X-ray detection elements, which is the peak value of the voltage signal from the waveform shaping circuit 63. For example, each pulse height discrimination circuit 65-*n* includes a comparison circuit 653-*n*. The voltage signal from the waveform shaping circuit 63 is input to one input terminal of each comparison circuit 653-*n*. Reference signals TH (reference voltage values) corresponding to different threshold values are supplied from the control device 18 to the other input terminals of the comparison circuits 653-*n*.

For example, a reference signal TH-1 is supplied to the comparison circuit 653-1 for an energy bin bin1, a reference signal TH-2 is supplied to the comparison circuit 653-2 for an energy bin bin2, and a reference signal TH-n is supplied to the comparison circuit 653-*n* for an energy bin binn. Each reference signal TH has an upper limit reference value and a lower limit reference value. Each comparison circuit 653-*n* outputs an electrical pulse signal when the voltage signal from the waveform shaping circuit 63 has a peak value corresponding to the energy bin corresponding to each reference signal TH. For example, if the peak value of the voltage signal from the waveform shaping circuit 63 is a peak value corresponding to the energy bin bin1 (if the peak value is between reference signals TH-1 and TH-2), the comparison circuit 653-1 outputs an electrical pulse signal. On the other hand, the comparison circuit 653-1 for the energy bin bin1 does not output an electrical pulse signal if the peak value of the voltage signal from the waveform shaping circuit 63 is not the peak value corresponding to the energy bin bin1. Further, if the peak value of the voltage signal from the waveform shaping circuit 63 is a peak value corresponding to the energy bin bin2 (when the peak value is between the reference signals TH-2 and TH-3), the comparison circuit 653-2 outputs an electrical pulse signal.

The counting circuit 67-*n* counts electrical pulse signals from the pulse height discrimination circuit 65-*n* at a readout cycle that matches a view switching cycle. For example, a trigger signal TS is supplied from the control device 18 to the counting circuit 67-*n* at a switching timing of each view. In response to supply of the trigger signal TS, the counting circuit 67-*n* adds 1 to a count number stored in an internal memory every time an electrical pulse signal is input from the pulse height discrimination circuit 65-*n*. In response to supply of the next trigger signal, the counting circuit 67-*n* reads data of the count number (i.e., count data) accumulated in the internal memory and supplies the data to the output circuit 69. Further, the counting circuit 67-*n* resets the count number accumulated in the internal memory to an initial value every time the trigger signal TS is supplied. In this manner, the counting circuit 67-*n* counts a count number for each view.

The output circuit 69 is connected to counting circuits 67-*n* for a plurality of readout channels mounted on the X-ray detector 15. For each of a plurality of energy bins, the output circuit 69 integrates the count data from the counting circuits 67-*n* for the plurality of readout channels to generate count data for the plurality of readout channels for each view. Count data of each energy bin is a set of data of count numbers defined by a channel, a segment (row), and an energy bin. The count data of each energy bin is transmitted to the console device 40 in units of views. The count data for each view is called a count data set CS. Further, the output circuit 69 transmits data detected for each pixel detected by the X-ray detector 15 to the console device 40. The detected data includes at least one of data detected for each pixel and count data for each energy bin.

Referring back to FIG. 1, the rotary frame 17 is an annular member that supports the X-ray tube 11, the wedge 12, the collimator 13, and the X-ray detector 15 in a facing manner. The rotary frame 17 is rotatably supported by a fixed frame around the subject P introduced therein. The rotary frame 17 further supports the DAS 16. Detection data output by the DAS 16 is transmitted through optical communication from a transmitter having light emitting diodes (LEDs) provided in the rotary frame 17 to a receiver having photodiodes provided in a non-rotating part (for example, a fixed frame) of the gantry 10 and transferred by the receiver to the console device 40. The method of transmitting the detection data from the rotary frame 17 to the non-rotating part is not limited to the method using optical communication described above, and any non-contact type transmitting method may be employed. The rotary frame 17 is not limited to an annular member and may be an arm-like member as long as it can support and rotate the X-ray tube 11 and the like.

The photon counting CT apparatus 1 is, for example, a rotate/rotate-type X-ray CT apparatus (a third generation CT) in which both the X-ray tube 11 and the X-ray detector 15 are supported by the rotary frame 17 and rotate around the subject P, but is not limited thereto and may be a stationary/rotate-type X-ray CT apparatus (a fourth generation CT) in which a plurality of X-ray detection elements arranged in an annular shape are fixed to a fixed frame and the X-ray tube 11 rotates around the subject P.

The control device 18 includes, for example, processing circuitry including a processor such as a central processing unit (CPU). The control device 18 receives an input signal from an input interface attached to the console device 40 or the gantry 10 and controls the operations of the gantry 10, the bed device 30, and the DAS 16. For example, the control device 18 rotates the rotary frame 17 or tilts the gantry 10. When tilting the gantry 10, the control device 18 rotates the rotary frame 17 about an axis parallel to the Z-axis direction on the basis of a tilt angle input to the input interface. The control device 18 ascertains the rotation angle of the rotary frame 17 according to the output of a sensor that is not shown, or the like. Further, the control device 18 controls the energy bins (reference signals TH) of the DAS 16. The control device 18 may be provided on the gantry 10 or may be provided on the console device 40.

<Bed Device 30>

The bed device 30 is a device on which the subject P to be scanned is placed and moved, and introduced into the rotary frame 17 of the gantry 10. The bed device 30 includes, for example, a base 31, a bed driving device 32, a top plate 33, and a support frame 34. The base 31 includes a housing that supports the support frame 34 such that the support frame 34 can move in the vertical direction (Y-axis direction). The bed driving device 32 includes a motor and an actuator. The bed driving device 32 moves the top plate 33 along the support frame 34 in the longitudinal direction of the top plate 33 (Z-axis direction). Further, the bed driving device 32 moves the top plate 33 in the vertical direction (Y-axis direction). The top plate 33 is a plate-shaped member on which the subject P is placed.

The bed driving device 32 may move not only the top plate 33 but also the support frame 34 in the longitudinal direction of the top plate 33. Further, contrary to the above, the gantry 10 may be movable in the Z-axis direction, and the rotary frame 17 may be controlled to come around the subject P by moving the gantry 10. Further, both the gantry 10 and the top plate 33 may be movable. Further, the photon counting CT apparatus 1 may be an apparatus in which the subject P is scanned in a standing or sitting position. In this case, the photon counting CT apparatus 1 includes a subject support mechanism instead of the bed device 30, and the gantry 10 rotates the rotary frame 17 about an axial direction perpendicular to the floor surface.

<Console Device 40>

The console device 40 includes, for example, a memory 41, a display 42, an input interface 43, a network connection circuit 44, and processing circuitry 50. Although the console device 40 will be described as being separate from the gantry 10 in the present embodiment, the gantry 10 may include some or all of the components of the console device 40.

The memory 41 is realized by, for example, a semiconductor memory element such as a random access memory (RAM) or a flash memory, a hard disk, an optical disc, or the like. The memory 41 stores, for example, detection data, projection data, reconstructed image data, CT image data, information regarding the subject P, imaging conditions, and the like. The memory 41 stores, for example, count data regarding a plurality of energy bins transmitted from the gantry 10. Such data may be stored in an external memory with which the photon counting CT apparatus 1 can communicate instead of the memory 41 (or in addition to the memory 41). The external memory is controlled by a cloud server that manages the external memory, for example, when the cloud server receives read/write requests.

The display 42 displays various types of information. For example, the display 42 displays a medical image (CT image) generated by the processing circuitry, a graphical user interface (GUI) image for receiving various operations by an operator such as a doctor or a technician, and the like. The display 42 is, for example, a liquid crystal display, a cathode ray tube (CRT), an organic electroluminescence (EL) display, or the like. The display 42 may be provided on the gantry 10. The display 42 may be of a desktop type, or may be a display device (for example, a tablet terminal) that can communicate wirelessly with the main body of the console device 40.

The input interface 43 receives various input operations of an operator, and outputs electrical signals indicating the content of the received input operations to the processing circuitry 50. For example, the input interface 43 receives input operations such as collection conditions at the time of collecting detection data or projection data, reconstruction conditions at the time of reconstructing a CT image, image processing conditions at the time of generating a post-processed image from a CT image, and energy bin setting conditions. For example, the input interface 43 is realized by a mouse, a keyboard, a touch panel, a track ball, a switch, a button, a joystick, a camera, an infrared sensor, a microphone, etc.

The input interface 43 may be provided in the gantry 10. Further, the input interface 43 may be realized by a display device (for example, a tablet terminal) that can communicate wirelessly with the main body of the console device 40. In this specification, the input interface is not limited to one that includes physical operation parts such as a mouse and a keyboard. For example, examples of the input interface include electrical signal processing circuitry that receives an electrical signal corresponding to an input operation from external input equipment provided separately from the device and outputs this electrical signal to a control circuit.

The network connection circuit 44 includes, for example, a network card having a printed circuit board, a wireless communication module, or the like. The network connection circuit 44 implements an information communication protocol depending on the type of network to be connected.

The processing circuitry 50 controls the overall operation of the photon counting CT apparatus 1, the operation of the gantry 10, and the operation of the bed device 30. The processing circuitry 50 executes, for example, a system control function 51, a preprocessing function 52, a reconstruction function 53, an image processing function 54, a scan control function 55, a display control function 56, a determination function 57, a removal function 58, and the like. These components are realized, for example, by a hardware processor (computer) executing a program (software) stored in the memory 41. The hardware processor is, for example, circuitry such as a CPU, a graphics processing unit (GPU), an ASIC, a programmable logic device (for example, a simple programmable logic device (SPLD) or a complex programmable logic device (CPLD), and a field programmable gate array (FPGA)), etc.

The program may be directly incorporated into the circuit of the hardware processor instead of being stored in the memory 41. In this case, the hardware processor realizes the functions by reading and executing the program incorporated into the circuit. The hardware processor is not limited to being configured as a single circuit, but may be configured as one hardware processor by combining a plurality of independent circuits to realize each function. Further, a plurality of components may be integrated into one hardware processor to realize each function.

The components included in the console device 40 or the processing circuitry 50 may be distributed and realized by a plurality of pieces of hardware. The processing circuitry 50 may be realized by a processing device that can communicate with the console device 40 instead of being a component included in the console device 40. The processing device is, for example, a workstation connected to one photon counting CT apparatus, or a device (e.g., a cloud server) that is connected to a plurality of photon counting CT apparatuses and collectively executes the same processing as that performed by the processing circuitry 50 described below.

The system control function 51 controls various functions of the processing circuitry 50 on the basis of input operations received by the input interface 43. The system control function 51 performs, for example, setting of energy bins, setting of ring determination and removal, and the like. The system control function 51 outputs setting conditions for the set energy bins to the control device 18.

The preprocessing function 52 performs preprocessing such as offset correction processing, inter-channel sensitivity correction processing, and beam hardening correction on detection data output by the DAS 16.

The reconstruction function 53 reconstructs a photon counting CT image regarding the subject P on the basis of detection data (count data). The reconstruction function 53 calculates the amount of X-ray absorption with respect to each of a plurality of reference materials on the basis of count data regarding a plurality of energy bins, the energy spectrum of X-rays incident on the subject P, and a response function representing detector response characteristics stored in the memory 41. Processing of obtaining the amount of X-ray absorption for each reference material in this manner is also called material discrimination. The reference materials can be set to any material such as calcium, calcification, bone, fat, muscle, air, organ, lesion, hard tissue, soft tissue, contrast material, etc. The reconstruction function 53 reconstructs a photon counting CT image representing a spatial distribution of a reference material to be imaged among the plurality of reference materials on the basis of the calculated amount of X-ray absorption for each of the plurality of reference materials and stores generated CT image data in the memory 41.

The image processing function 54 converts the CT image data into three-dimensional image data or cross-sectional image data of an arbitrary cross section using a known method on the basis of an input operation received by the input interface 43. Conversion into three-dimensional image data may be performed by the preprocessing function 52.

The scan control function 55 controls detection data collection processing in the gantry 10 by instructing the X-ray high voltage device 14, the DAS 16, the control device 18, and the bed driving device 32. The scan control function 55 controls operations of each part at the time of capturing for collecting positioning images and capturing images used for diagnosis.

The display control function 56 causes the display 42 to display medical images (CT images) generated by the processing circuitry, GUI images for receiving various operations of an operator such as a doctor or a technician, and the like.

The determination function 57 and the removal function 58 perform processing for removing or reducing a ring artifact from an image (hereinafter referred to as a "counting image") generated on the basis of sum data of photon detection results of a plurality of different X-ray energy bands (data obtained by summing count data for each energy bin). The counting image is an image that does not have energy information, like a conventional CT image.

The determination function 57 performs first determination processing of determining spike components in a counting image generated on the basis of sum data of photon detection results in a plurality of different X-ray energy bands obtained by the photon counting CT apparatus 1 and second determination processing of determining a ring artifact (for example, presence or absence of a ring artifact) on the basis of a plurality of energy images (for example, bin images) generated on the basis of photon detection results for each different X-ray energy band. The counting image and the bin images are, for example, images reconstructed by the reconstruction function 53. The determination function 57 determines, among the spike components determined in the first determination processing, a spike component whose position corresponds to the ring artifact determined in the second determination processing as a ring artifact in the counting image. Details of processing of the determination function 57 will be described later. The determination function 57 is an example of a "determination unit."

The removal function 58 removes or reduces a ring artifact in the counting image on the basis of both the result of the first determination processing and the result of the second determination processing performed by the determination function 57. The removal function 58 removes or reduces the ring artifact in the counting image by subtracting the determined ring artifact in the counting image from the counting image. Details of processing of the removal function 58 will be described later. The removal function 58 is an example of a "removal unit."

According to the above-described configuration, the photon counting CT apparatus 1 scans the subject P in a scanning mode such as helical scanning, conventional scanning, or step-and-shoot. Helical scanning is a mode in which the subject P is scanned in a spiral manner by rotating the rotary frame 17 while moving the top plate 33. Conventional scanning is a mode in which the rotary frame 17 is rotated while the top plate 33 is kept stationary to scan the subject P in a circular orbit. Step-and-shoot is a mode in which the position of the top plate 33 is moved at regular intervals to perform conventional scanning in a plurality of scanning areas.

[Processing Flow]

Figure 3:
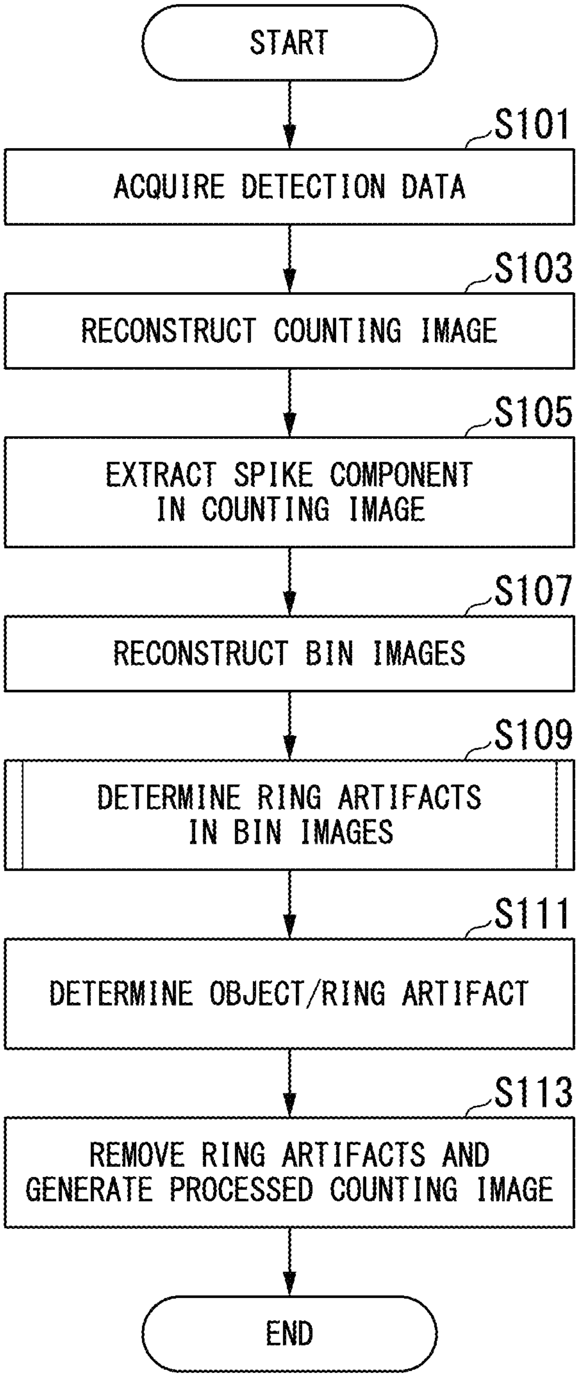
FIG. 3 is a flowchart showing an example of ring artifact removal processing of the photon counting CT apparatus 1 according to the first embodiment.

Next, a series of flows in ring artifact removal processing of the photon counting CT apparatus 1 will be described. FIG. 3 is a flowchart showing an example of ring artifact removal processing of the photon counting CT apparatus 1 according to the first embodiment. The ring artifact removal processing shown in FIG. 3 is started, for example, when an operator inputs a ring artifact removal instruction via the input interface 43 during or after scanning the subject P. Alternatively, this ring artifact removal processing may be incorporated into a series of photon counting CT image reconstruction processing and automatically executed.

First, the processing circuitry 50 of the console device 40 acquires the detection data output by the DAS 16 (step S101). This detection data includes count data for each energy bin counted by the DAS 16 (results of detection of photons of a plurality of different X-ray energy bands).

Subsequently, the reconstruction function 53 reconstructs a counting image on the basis of data obtained by summing the acquired count data for each energy bin (step S103).

Subsequently, the determination function 57 performs first determination processing of extracting spike components (determining spike components) in the reconstructed counting image (step S105). A spike component indicates a local area where a pixel value (CT value) is significantly different from other areas. For example, the determination function 57 uses the pixel value of each pixel of the reconstructed counting image, and extracts spike components on the basis of degrees of differences between the pixel value and pixel values of adjacent pixels. The spike components are caused either by a ring artifact or by an object to be imaged (e.g., an organ, a bone, or the like).

Subsequently, the reconstruction function 53 reconstructs a plurality of bin images on the basis of the acquired count data for each energy bin (step S107).

Subsequently, the determination function 57 performs second determination processing of determining ring artifacts on the basis of the plurality of reconstructed bin images (step S109). For example, the determination function 57 performs spike component determination for determining a ring artifact on the basis of a spike component of each bin image or CT value ratio determination for determining a ring artifact on the basis of a CT value ratio of each bin image.

<Ring Artifact Determination Processing (Spike Component Determination)>

Figure 4:
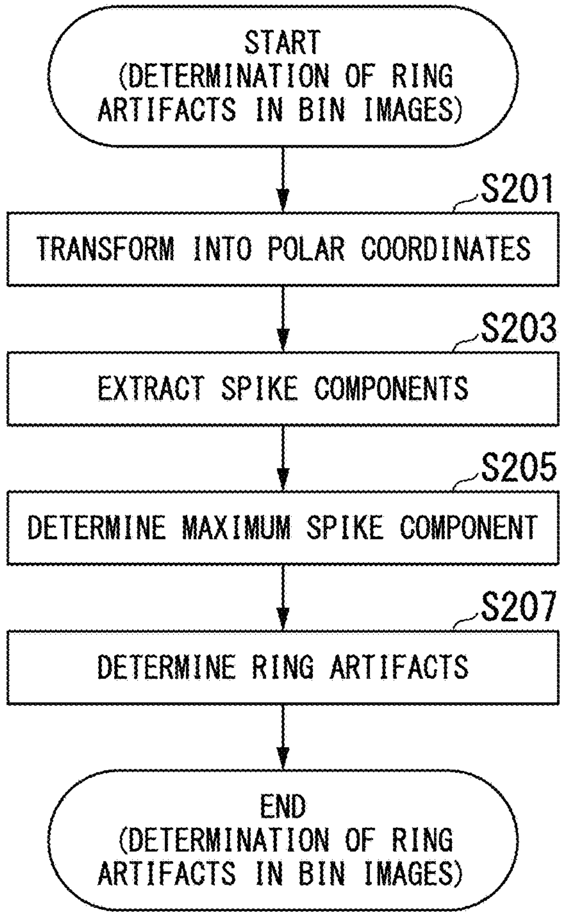
FIG. 4 is a flowchart showing an example of ring artifact determination processing (spike component determination) of the photon counting CT apparatus 1 according to the first embodiment.
Figure 5:
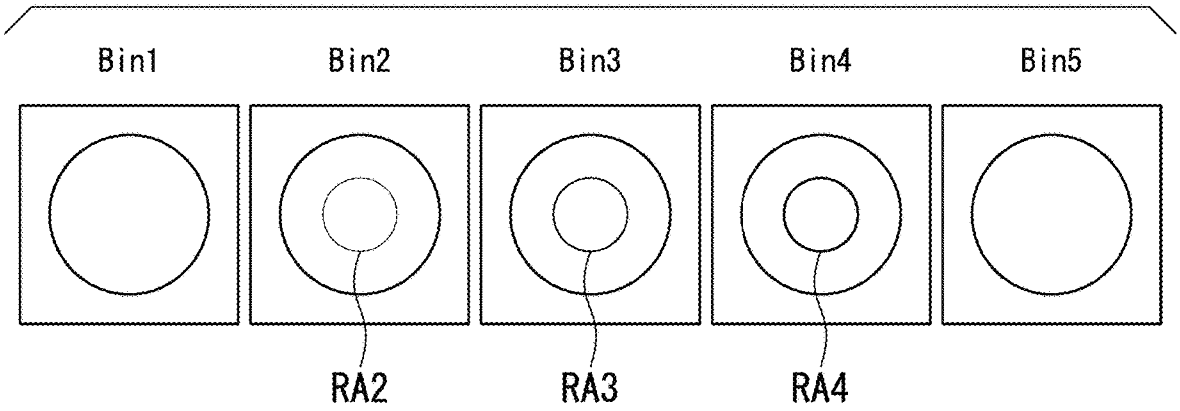
FIG. 5 is a diagram showing a state in which a ring artifact occurs in each bin image according to the first embodiment.

FIG. 4 is a flowchart showing an example of ring artifact determination processing (spike component determination) of the photon counting CT apparatus 1 according to the first embodiment. FIG. 5 is a diagram showing a state in which a ring artifact occurs in each bin image according to the first embodiment. FIG. 5 shows five bin images Bin1 to Bin5 corresponding to five energy bins. Among these, ring artifacts RA2, RA3, and RA4 appear in three bin images Bin2, Bin3, and Bin4, and ring artifacts do not appear in two bin images Bin1 and Bin5. Furthermore, the ring artifacts RA2, RA3, and RA4 appear strongly and clearly in the order of bin image Bin2, bin image Bin3, and bin image Bin4.

In the present embodiment, a ring artifact due to a temporary output failure caused by temperature dependence of detection elements is mainly targeted for determination. The present embodiment can also be used to detect a ring artifact caused by a non-comfortable pixel (NCP, also referred to as a "defective element") that suddenly occurs in the X-ray detector 15. For artifacts caused by such a non-comfortable pixel, the position (map) of the non-comfortable pixel may be recorded in advance and data of a pixel corresponding to the non-comfortable pixel may be corrected by a method such as adjacent interpolation.

Figure 6:
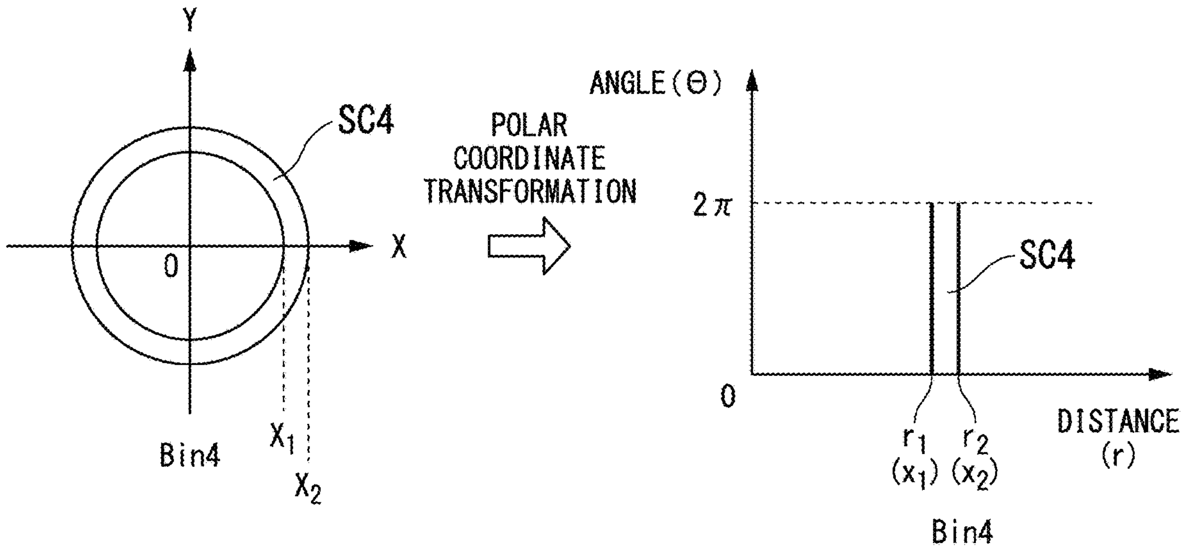
FIG. 6 is a diagram illustrating polar coordinate transformation processing for the bin image according to the first embodiment.

In order to determine ring artifacts as described above, the determination function 57 first performs polar coordinate transformation on each bin image represented in orthogonal coordinates (step S201). FIG. 6 is a diagram illustrating polar coordinate transformation processing for a bin image according to the first embodiment. In the example of FIG. 6, the bin image Bin4 (having the origin O at the center of the image) represented on orthogonal coordinates (XY plane) is transformed into polar coordinates in which it is represented by a distance (r) from the origin O and a rotation angle (angle θ) from a predetermined axis (e.g., Y axis) having the origin O as a center. Here, if a ring artifact occurs in the bin image Bin4, for example, a spike component SC4 will occur at a position corresponding to this ring artifact in the polar coordinate-transformed bin image Bin4. For example, this spike component SC4 occurs between X coordinates X1 and X2 on the XY plane and occurs between distances r1 and r2 on the polar coordinates.

The determination function 57 extracts spike components by applying, for example, a high frequency filter to the bin image after polar coordinate transformation (step S203). A spike component corresponding to a ring component appears at a position at a predetermined distance (r1 to r2) from the origin O on the polar coordinates as a region having a different pixel value from other regions in the direction of the angle θ. The determination function 57 extracts a spike component corresponding to such a ring component. Any method such as image processing may be employed to extract spike components.

Subsequently, the determination function 57 determines a maximum spike component by comparing pixel values of spike components extracted from respective bin images between bin images (step S205). For example, the determination function 57 compares pixel values (first pixel values) at a position (first position) of a spike component extracted in a certain bin image (first bin image) among a plurality of bin images with pixel values (second pixel values) at the same position (first position) in each of other bin images, and determines the largest pixel value at the same position (first position) as the maximum spike component.

Subsequently, the determination function 57 determines whether the extracted spike components are caused by ring artifacts on the basis of the result of comparison between the maximum spike component and a predetermined threshold value (step S207). The determination function 57 determines a ring artifact on the basis of the following formulas (1) and (2), for example.

[Math. 1]

$$\text{IF}(\text{Spike\_max}[x,y]>\text{Spike}[x,y,E]*A)\rightarrow\text{Spike\_max}[x,y]=\text{ring component} \quad \text{Formula (1)}$$

$$\text{IF}(\text{Spike\_max}[x,y]=\text{ring component})\rightarrow\text{Spike}[x,y,E]=\text{ring component} \quad \text{Formula (2)}$$

In the above formula (1), Spike_max[x,y] is the maximum spike component, Spike[x,y,E] is the spike component for each bin image (for each energy band E), and A (A>1) is a parameter. Here, when the maximum value of spike components extracted in a certain bin image (maximum spike component) is greater than the predetermined threshold value (if the IF statement of formula (1) is satisfied, that is, the maximum spike component is greater than spike components×A of other bin images), the determination function 57 determines that the maximum spike component is a ring component (caused by a ring artifact). Then, upon determining that the maximum spike component is a ring component, the determination function 57 determines that spike components in all other bin images at the same position (same pixel) are also ring components (caused by ring artifacts) in the above formula (2). The parameter A can be arbitrarily set such that a ring component can be determined according to imaging conditions and the like.

The determination function 57 may calculate differences (=first pixel values−second pixel values) or ratios (=first pixel values/second pixel values) between pixel values (first pixel values) at the position (first position) of a spike component extracted in a certain bin image (first bin image) among the plurality of bin images and pixel values (second pixel values) at the same position (first position) in each of the other bin images, and determine the maximum difference or ratio among the calculated differences or ratios as the maximum spike component. Here, when the maximum value of spike components (maximum spike component) extracted in a certain bin image is greater than the predetermined threshold value, the determination function 57 may determine that the maximum spike component is a ring component. Then, upon determining that the maximum spike component is a ring component, the determination function 57 may determine that spike components in all other bin images at the same pixel are also ring components. Accordingly, processing of the flowchart of spike component determination shown in FIG. 4 ends.

That is, in second determination processing, the determination function 57 (determination unit) transforms each of the plurality of energy images represented in orthogonal coordinates into polar coordinates, extracts spike components from each of the plurality of energy images subjected to polar coordinate transformation, and determines ring artifacts on the basis of the spike components. In addition, in second determination processing, the determination function 57 (determination unit) calculates an index value regarding the first spike component (maximum spike component) on the basis of results of comparison between the first spike component extracted at the first position of the first energy image among the plurality of energy images and pixel values at the first position in other energy images, and determines whether the first spike component is caused by a ring artifact on the basis of a result of comparison between the index value and the threshold value. The plurality of energy images are bin images reconstructed using photon detection results for each of plurality of different X-ray energy bands.

<Ring Artifact Determination Processing (CT Value Ratio Determination)>

Figure 7:
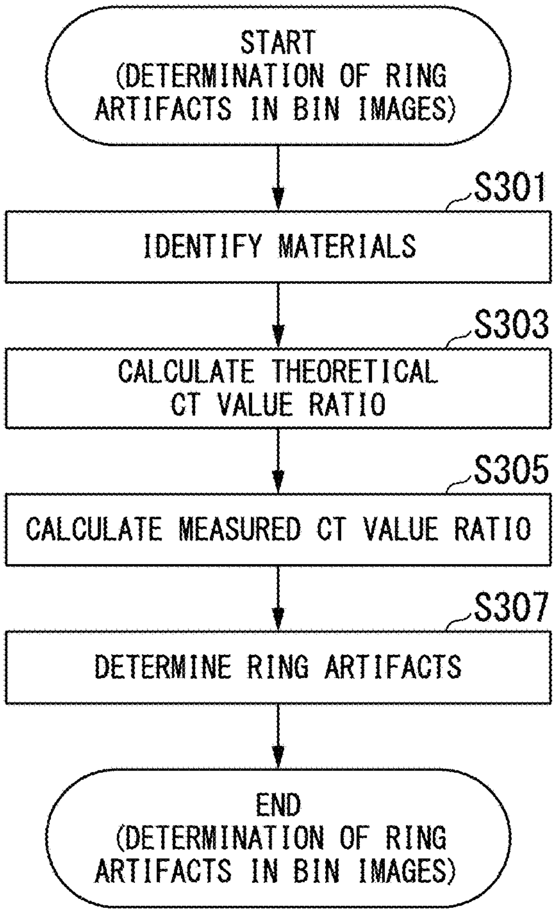
FIG. 7 is a flowchart showing an example of ring artifact determination processing (CT value ratio determination) of the photon counting CT apparatus 1 according to the first embodiment.

FIG. 7 is a flowchart showing an example of ring artifact determination processing (CT value ratio determination) of the photon counting CT apparatus 1 according to the first embodiment. First, the determination function 57 identifies materials (reference materials) from a threshold value of CT values of each bin image and a ratio (K-edge) for each energy bin (step S301). The determination function 57 identifies reference materials such as water, calcium, iodine, and gadolinium for each pixel position of each bin image, for example. Alternatively, the determination function 57 may identify reference materials using a machine learning technique such as a neural network.

Figure 8:
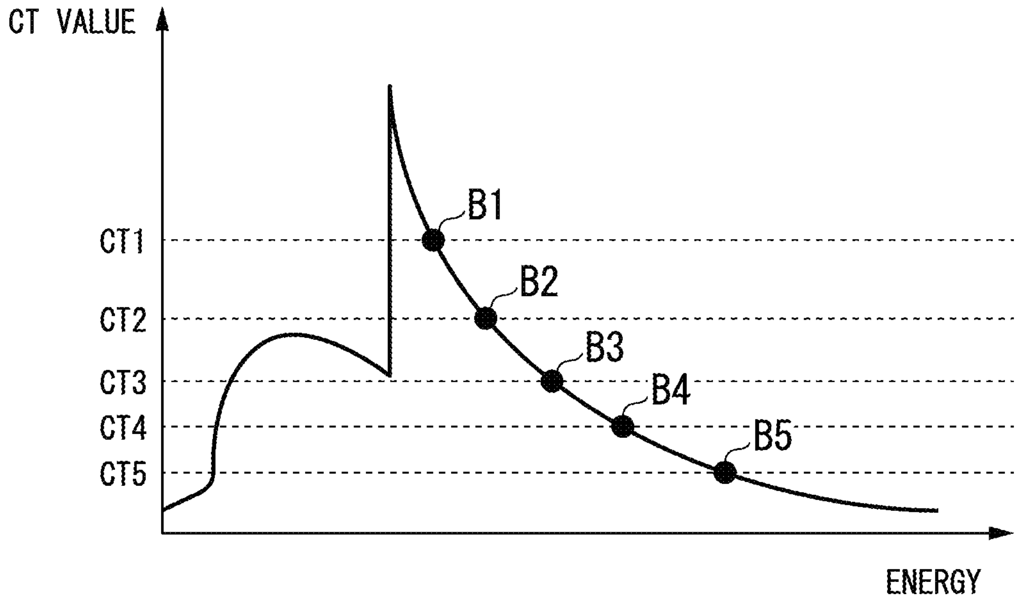
FIG. 8 is a graph showing a relationship between a theoretical energy value and a CT value of a reference material according to the first embodiment.

Subsequently, the determination function 57 calculates a plausible theoretical CT value ratio (theoretical CT value ratio) in each bin image for each identified material from a mass attenuation coefficient (step S303). FIG. 8 is a graph showing the relationship between a theoretical energy value and a CT value of a reference material according to the first embodiment. FIG. 8 shows, for example, a theoretical curve (mass attenuation coefficient) showing the relationship between the energy and CT value regarding iodine at a predetermined concentration. On the theoretical curve in this example, CT values of energies B1 to B5 corresponding to five energy bins are CT1 to CT5. The determination function

57 calculates, for example, CT2/CT1, CT3/CT1, CT4/CT1, and CT5/CT1 as CT value ratios on the basis of the CT value of the energy B1.

Referring back to FIG. 7, the determination function 57 calculates a CT value ratio (measured CT value ratio) based on the measured value at each pixel of each bin image (step S305). The determination function 57 calculates, for example, CT2_*r*/CT1_*r*, CT3_*r*/CT1_*r*, CT4_*r*/CT1_*r*, and CT5_*r*/CT1_*r* as measured CT value ratios on the basis of the CT value (CT1_*r*) of the bin image Bin1.

Subsequently, the determination function 57 determines whether an extracted spike component is caused by a ring artifact on the basis of a result of comparison between the theoretical CT value ratio and the measured CT value ratio (step S307). The determination function 57 determines that the extracted spike component is caused by a ring artifact when there is a deviation equal to or greater than a predetermined threshold value between the theoretical CT value ratio and the measured CT value ratio. The determination function 57 determines a ring artifact on the basis of the following formulas (3) to (8).

[Math. 2]

$$CT_{ideal}[En] = \frac{\mu m_{iodine}[E_n] \times \rho - \mu m_{water}[E_n]}{\mu m_{water}[E_n]} \times 1000[HU] \quad \text{Formula (3)}$$

$$\text{CT\_ratio}[E_n](\text{theoretical}) = \frac{CT_{ideal}[E_0]}{CT_{ideal}[E_n]} \quad \text{Formula (4)}$$

$$\text{CT\_ratio}_m[x, y, E_n](\text{atually measured}) = \frac{CT_{measure}[x, y, E_0]}{CT_{measure}[x, y, E_n]} \quad \text{Formula (5)}$$

If (a < $\text{CT\_ratio}_m[x, y, E_n]$ < b){
$CT_{measure}[x, y, E_n] \neq$ ring component
}else{
$CT_{measure}[x, y, E_n] =$ ring component
} Formula (6)

$a = \text{CT\_ratio}[E_n] - \alpha$ Formula (7)

$b = \text{CT\_ratio}[E_n] + \alpha$ Formula (8)

In the above formula (3), $CT_{ideal}[En]$ is a theoretical CT value for each energy band E, $\mu m_{iodine}[En]$ is the mass attenuation coefficient of iodine for each energy band E, $\mu m_{water}[En]$ is the mass attenuation coefficient of water for each energy band E, and p is concentration. In the above formula (4), CT_ratio[En] is a theoretical CT value ratio for each energy band E. In the above formula (5), CT_ratiom [x,y,En] is a measured CT value ratio for each energy band E, and $CT_{measure}[x,y,En]$ is a measured CT value for each energy band E. Here, if a measured CT value ratio calculated in a certain bin image is included in a predetermined range (if the IF statement of formula (6) is satisfied, that is, if the measured CT value ratio is greater than a threshold value a and less than a threshold value b), the determination function 57 determines that the measured CT value is not a ring component (is not caused by a ring artifact). On the other hand, here, if a measured CT value ratio calculated in a certain bin image is not included in the predetermined range (if the IF statement of formula (6) is not satisfied, that is, if the measured CT value ratio is equal to or less than the threshold value a or equal to or greater than the threshold value b), the determination function 57 determines that the measured CT value is a ring component (caused by a ring artifact). The threshold values a and b are defined by the above formulas (7) and (8), and a is a parameter. The parameter a can be arbitrarily set such that a ring component can be determined depending on imaging conditions and the like. With the above-described processes, processing of the flowchart of spike component determination shown in FIG. 7 ends.

That is, in second determination processing, the determination function 57 (determination unit) identifies materials included in a plurality of energy images on the basis of the plurality of energy images, and determines a ring artifact on the basis of results of comparison between theoretical pixel values which are theoretical values calculated from the mass attenuation coefficients of the identified materials and measured pixel values which are measured values calculated from the plurality of energy images.

Furthermore, in second determination processing, the determination function 57 (determination unit) determines whether ring components included in the plurality of energy images are caused by ring artifacts on the basis of results of comparison between differences between ratios between a plurality of theoretical pixel values corresponding to a plurality of predetermined energy values and ratios between a plurality of measured pixel values corresponding to the plurality of predetermined energy values, and threshold values.

Referring back to FIG. 3, the determination function 57 determines an object/ring artifact for each spike component extracted in the counting image in step S105 on the basis of the result of determination of the ring component in each bin image in step S109 (step S111). That is, the determination function 57 determines, among the spike components extracted from the counting image in step S105, a spike component whose position corresponds to that determined to be a ring component in step S109, to be a ring component (to be caused by a ring artifact). On the other hand, the determination function 57 determines, among the spike components extracted from the counting image in step S105, a spike component whose position does not correspond to that determined to be a ring component in step S109 to be an object component (to be caused by an object).

Subsequently, the removal function 58 removes or reduces ring artifacts from the counting image on the basis of the object/ring artifact determination result and generates a processed counting image (step S113). For example, the removal function 58 generates the processed counting image by subtracting the determined ring component from the original counting image. Accordingly, processing of the flowchart shown in FIG. 3 ends.

According to the first embodiment described above, ring artifacts in photon counting CT images can be determined and removed with high accuracy. In particular, it is possible to detect and remove ring artifacts that cannot be determined to be objects and removed using conventional methods. Furthermore, the configuration of the present embodiment can be flexibly applied to determination and removal of ring artifacts caused by non-comfortable pixels that suddenly occur in the X-ray detector.

Second Embodiment

Next, a second embodiment will be described. Although a configuration in which ring artifacts are determined and removed using a bin image for each energy bin has been described in the first embodiment, ring artifacts are determined and removed using a virtual monochromatic image (also referred to as a "Mono keV image") in the second embodiment. A virtual monochromatic image is an image corresponding to any virtual monochromatic X-ray energy. A virtual monochromatic image is a type of spectral image. Each device configuration of the second embodiment is common to the first embodiment. The second embodiment will be described below, focusing on differences from the first embodiment.

[Processing Flow]

Figure 9:
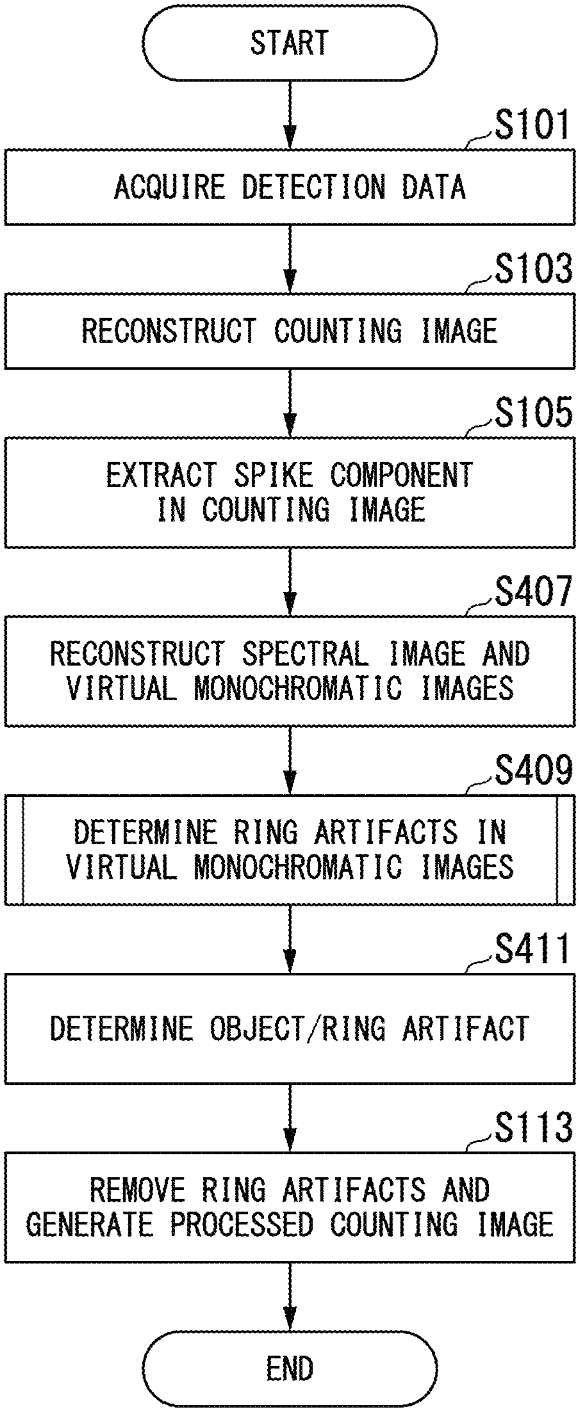
FIG. 9 is a flowchart showing an example of ring artifact removal processing of a photon counting CT apparatus 1 according to a second embodiment.

Hereinafter, a series of flows of ring artifact removal processing of the photon counting CT apparatus 1 will be described. FIG. 9 is a flowchart showing an example of ring artifact removal processing of the photon counting CT apparatus 1 according to the second embodiment. The ring artifact removal processing shown in FIG. 9 is started, for example, when the operator inputs a ring artifact removal instruction via the input interface 43 during or after scanning the subject P. Alternatively, this ring artifact removal processing may be incorporated into a series of photon counting CT image reconstruction processing and automatically executed.

First, the processing circuitry 50 of the console device 40 acquires detection data output by the DAS 16 (step S101). This detection data includes count data for each energy bin counted by the DAS 16 (results of detection of photons of a plurality of different X-ray energy bands).

Subsequently, the reconstruction function 53 reconstructs a counting image on the basis of data obtained by summing the acquired count data for each energy bin (step S103).

Subsequently, the determination function 57 performs first determination processing of extracting spike components (determining spike components) in the reconstructed counting image (step S105). For example, the determination function 57 uses the pixel value of each pixel of the reconstructed counting image, and extracts spike components on the basis of degrees of differences between the pixel value and pixel values of adjacent pixels.

Subsequently, the reconstruction function 53 reconstructs a spectral image (reference material image) and virtual monochromatic images corresponding to a plurality of energy values on the basis of the acquired count data for each energy bin (step S407). The reconstruction function 53 generates a plurality of types of reference material projection data from bin projection data for each of a plurality of energy bands as material decomposition processing from the detection data (count data for each energy bin), and generates a reference material image therefrom. Further, the reconstruction function 53 reconstructs a plurality of virtual monochromatic images corresponding to a plurality of energy values (e.g., 40 keV, 50 keV, . . . NkeV) using the reference material image. The plurality of virtual monochromatic images are virtual monochromatic X-ray energy images reconstructed using photon detection results for a plurality of different X-ray energy bands.

Next, the determination function 57 performs second determination processing of determining a ring artifact on the basis of the plurality of reconstructed virtual monochromatic images (step S409). For example, the determination function 57 performs spike component determination for determining a ring artifact on the basis of a spike component of each virtual monochromatic image, or CT value ratio determination for determining a ring artifact on the basis of a CT value ratio of each virtual monochromatic image. Such spike component determinations and CT value ratio determinations are similar to processing for bin images in the first embodiment.

Subsequently, the determination function 57 determines an object/ring artifact for each spike component extracted in the counting image in step S105 on the basis of the result of determination of a ring component in each virtual monochromatic image in step S409 (step S411). That is, the determination function 57 determines, among the spike components extracted from the counting image in step S105, a spike component whose position corresponds to that determined to be a ring component in step S409 to be a ring component (to be caused by a ring artifact). On the other hand, the determination function 57 determines, among the spike components extracted from the counting image in step S105, a spike component whose position does not correspond to that determined to be a ring component in step S409 to be an object component (to be caused by an object).

Subsequently, the removal function 58 removes or reduces ring artifacts from the counting image on the basis of the object/ring artifact determination result, and generates a processed counting image (step S113). For example, the removal function 58 generates the processed counting image by subtracting the determined ring component from the original counting image. Accordingly, processing of the flowchart shown in FIG. 9 ends.

According to the second embodiment described above, ring artifacts in photon counting CT images can be determined and removed with high accuracy. In particular, it is possible to detect and remove ring artifacts that cannot be determined to be objects and removed using conventional methods. Furthermore, the configuration of the present embodiment can be flexibly applied to determination and removal of ring artifacts caused by no-comfortable pixels that suddenly occur in the X-ray detector.

According to the embodiments described above, it is possible to determine and remove ring artifacts in photon counting CT images with high accuracy by including a determination unit (determination function 57) that performs first determination processing of determining spike components in a counting image generated on the basis of sum data of photon detection results for a plurality of different X-ray energy bands and second determination processing of determining ring artifacts on the basis of a plurality of energy images generated on the basis of a photon detection result for each of the plurality of different X-ray energy bands, and a removal unit (removal function 58) that removes or reduces ring artifacts in the counting image on the basis of both the result of the first determination processing and the result of the second determination processing.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A photon counting CT apparatus, comprising:

processing circuitry configured to:

perform first determination processing of determining spike components in a counting image generated based on sum data of photon detection results for a plurality of different X-ray energy bands and second determination processing of determining ring artifacts based on a plurality of energy images generated based on a photon detection result for each of the plurality of different X-ray energy bands; and remove or reduce ring artifacts in the counting image based on both a result of the first determination processing and a result of the second determination processing, wherein, in the second determination processing, the processing circuitry is further configured to:

identify materials included in the plurality of energy images based on the plurality of energy images; and determine the ring artifacts based on results of comparison between theoretical pixel values, which are theoretical values calculated from mass attenuation coefficients of the identified materials, and measured pixel values, which are measured values calculated from the plurality of energy images.

2. The photon counting CT apparatus according to claim 1, wherein, in the second determination processing, the processing circuitry is further configured to:

determine whether ring components included in the plurality of energy images are caused by the ring artifacts based on results of comparison of differences between ratios between the plurality of theoretical pixel values corresponding to a plurality of predetermined energy values and ratios between the plurality of measured pixel values corresponding to the plurality of energy values with a threshold value.

3. The photon counting CT apparatus according to claim 1, wherein the processing circuitry is further configured to:

determine, among the spike components determined in the first determination processing, a spike component whose position corresponds to a ring artifact determined in the second determination processing, as a ring artifact in the counting image; and remove or reduce ring artifacts in the counting image by subtracting the determined ring artifact in the counting image from the counting image.

4. The photon counting CT apparatus according to claim 1, wherein the plurality of energy images are bin images reconstructed using photon detection results for each of the plurality of different X-ray energy bands.

5. The photon counting CT apparatus according to claim 1, wherein the plurality of energy images are virtual monochromatic X-ray energy images reconstructed using photon detection results for each of the plurality of different X-ray energy bands.

6. A medical image processing method, using a computer, the method comprising:

performing first determination processing of determining spike components in a counting image generated based on sum data of photon detection results for a plurality of different X-ray energy bands and second determination processing of determining ring artifacts based on a plurality of energy images generated based on a photon detection result for each of the plurality of different X-ray energy bands; and removing or reducing ring artifacts in the counting image based on both a result of the first determination processing and a result of the second determination processing, wherein the step of performing the second determination processing further comprises:

identifying materials included in the plurality of energy images based on the plurality of energy images; and determining the ring artifacts based on results of comparison between theoretical pixel values, which are theoretical values calculated from mass attenuation coefficients of the identified materials, and measured pixel values, which are measured values calculated from the plurality of energy images.

* * * * *